United States Patent [19]

Nowak

[11] Patent Number: 5,693,849
[45] Date of Patent: Dec. 2, 1997

[54] AQUEOUS SYNTHESIS OF IODOPROPARGYL CARBAMATE

[75] Inventor: Milton Nowak, South Orange, N.J.

[73] Assignee: Troy Corporation, Florham Park, N.J.

[21] Appl. No.: 741,037

[22] Filed: Oct. 30, 1996

[51] Int. Cl.$^6$ ................................................. C07C 261/00
[52] U.S. Cl. .................... 560/167; 560/22; 560/25; 560/27; 560/33; 560/115; 560/158
[58] Field of Search .................... 560/158, 167, 560/25, 33, 115, 22, 27

[56] References Cited

U.S. PATENT DOCUMENTS

| | | |
|---|---|---|
| 3,923,870 | 12/1975 | Singer . |
| 4,297,258 | 10/1981 | Long, Jr. . |
| 4,474,807 | 10/1984 | Gerhardt et al. . |
| 4,725,680 | 2/1988 | Barcelo et al. . |
| 4,841,088 | 6/1989 | Kusaba et al. . |
| 5,183,927 | 2/1993 | Utsunomiya et al. . |
| 5,194,660 | 3/1993 | Leung et al. . |
| 5,321,151 | 6/1994 | Lange . |
| 5,326,899 | 7/1994 | Lange . |

FOREIGN PATENT DOCUMENTS

| | | |
|---|---|---|
| 0 014 032 | 8/1980 | European Pat. Off. . |
| 0 015 044 | 9/1980 | European Pat. Off. . |
| 0 513 541 A2 | 11/1992 | European Pat. Off. . |
| 0 539 092 A1 | 4/1993 | European Pat. Off. . |
| 33 04 899 A1 | 8/1984 | Germany . |
| 3390987 A1 | 3/1991 | Germany . |
| 230119 | 10/1968 | U.S.S.R. . |
| 1 455 043 | 7/1974 | United Kingdom . |

OTHER PUBLICATIONS

Sladkov et al., "Synthesis and Spectra of Iodo- and Bromoactylenic Derivatives", *J. Org. Chem. of the USSR*, 1(3):406–411 (1965).

*Primary Examiner*—Michael L. Shippen
*Attorney, Agent, or Firm*—Banner & Witcoff Ltd.

[57] ABSTRACT

This invention is directed to a method for making an iodopropargyl carbamate in an aqueous reaction medium so as to yield a more pure and stable, e.g., U.V. resistant, product in a high yield, free from environmental hazards posed by using non-aqueous solvents as the reaction medium.

13 Claims, No Drawings

AQUEOUS SYNTHESIS OF IODOPROPARGYL CARBAMATE

BACKGROUND OF THE INVENTION

1. Field of the Invention

This invention concerns a new method of manufacturing an iodoalkynyl carbamate and especially an iodopropargyl carbamate. The invention is particularly aimed at a method of making an iodopropargyl carbamate in an aqueous reaction medium so as to yield a more pure and stable, e.g., U.V. resistant, product in a high yield, free from environmental hazards posed by using non-aqueous solvents as the reaction medium.

2. Description of Related Art

Iodopropargyl butyl carbamate (IPBC) was first described in U.S. Pat. No. 3,923,870 and is an extremely effective fungicide used to prevent mildew growth in coatings prepared from oil-based and water-based paints. It also is used widely for wood preservation, in metal working fluids and other applications where it is desirable to protect a surface or a liquid composition from the discoloring and destructive effects of fungal growth.

The method for preparing IPBC, described in the aforementioned U.S. Pat. No. , requires an initial preparation of iodopropargyl alcohol. This is a dangerous compound that must be isolated by extraction in ethyl ether. The ether then must be evaporated to yield the pure alcohol product. Iodopropargyl alcohol is not only extremely corrosive to the skin, but also decomposes, possibly violently, at a temperature of about 125° C., so it must be very carefully handled. To form the final IPBC product, iodopropargyl alcohol then is reacted with butyl isocyanate, which also is a strong irritant. As prepared, the iodopropargyl carbamate material is very impure, possesses an undesirable odor, and requires several recrystallizations to produce a product which demonstrates a definite melting point.

European Patent Publication No. 0014032 describes another method of preparing IPBC. Propargyl alcohol first is reacted with an isocyanate, e.g., butyl isocyanate, to form propargyl butyl carbamate. The propargyl butyl carbamate then is reacted with a slight molar excess of an iodinating agent such as a mixture of iodine, an alkali metal hydroxide and sodium hypochlorite in an aqueous medium, typically containing a co-solvent. To promote sufficient contact between the sparingly water-soluble alkynyl carbamate and the iodinating agent, the reaction preferably is conducted in the presence of a water miscible auxiliary solvent such as an alcohol, e.g., an aqueous methanol solution. The method of isolating the end product is by extraction from the aqueous methanol solution with an immiscible solvent. This document also suggests conducting the reaction in an aqueous medium by initially dispersing or emulsifying the alkynyl carbamate, with the aid of a surfactant, but does not indicate the ultimate method of product isolation, the yield, nor the purity of the product made in this manner. (See Examples 4 and 5). Surfactants disclosed as being suitable include hydrolyzed or partially hydrolyzed polyvinyl acetates, phase-transfer catalysts such as cetyl trimethyl ammonium bromide, dispersing agents such as the sodium salt of a condensate of formaldehyde and naphthalene sulfonic acid and emulsifying agents such as ethoxylated nonyl phenols.

In this EP publication, the presence of the iodopropargyl butyl carbamate (IPBC) is ascertained merely by infrared (IR) spectra. Viewed in the light of present day requirements, both commercial and regulatory, this data does not document the completion of the reaction. The appearance of an infrared absorption band at 2200 $cm^{-1}$ also does not indicate the yield, nor the purity of the end product. There are no statements in EP 0014032 (examples 4 and 5) that a high product yield (i.e., above 90%) was obtained.

U.S. Pat. No. 4,297,258 similarly describes the reaction of propargyl butyl carbamate with iodine in an aqueous medium containing a co-solvent (without a surfactant), but the product again is extracted from the reaction mixture with a water immiscible organic solvent. The quality of the product is not described, nor is the yield. There is also described, in terms almost identical to EP14032, the reaction of propargyl butyl carbamate with iodine in an aqueous solution in the presence of a protective colloid or a dispersing agent (e.g., a surfactant). As with the EP publication, there is no mention of yield and purity.

Attempts to replicate the procedures described in the aforementioned patents have demonstrated yields only from about 50 to 78% and a purity not greater than about 90%. The products formed by the procedures described in these disclosures, using an aqueous medium free of co-solvent, are brown sludgy masses that do not lend themselves to easy filtration or isolation except by extraction with water immiscible solvents.

There is, of course, no question that the overall product yield in a commercial process is of great economic importance. This is especially true when dealing with relatively high priced materials such as iodine and butyl isocyanate.

There is, however, another at least equally significant consideration, and that is product purity. In the case of pesticides, such as fungicides, U.S. regulatory clearance procedures require the identification of, and toxicological studies for, any single impurity present in an amount of more than 0.1 wt. %. Production of very high purity material is, therefore, necessary to reduce the costs associated with the registration of a pesticide with the EPA. Perhaps of equal importance, is the effect residual impurities have on the long term stability of a product. Not only must the amount of impurities be considered, but also their nature. Especially with IPBC, the presence of even trace impurities has been observed to cause product instability that often is reflected in a degradation in product color, i.e., product discoloration.

I have discovered, as a completely unexpected result of the inventive method, that the end product, IPBC, of the claimed method contains substantially less di-iodo-compounds and substantially less tri-iodo-compounds than products prepared in an aqueous methanol solution. For instance, products prepared by direct iodination of propargyl butyl carbamate in an aqueous methanol solution usually contain from about 0.25–0.35% by weight of polyiodinated materials, that is, an iodopropynyl butyl carbamate molecule containing from 2 to 3 iodine atoms. Such poly-iodinated molecules are relatively unstable to light, and release iodine under UV exposure, contributing to the discoloration of the product and the discoloration of any composition containing the product.

It has been observed that IPBC of a low purity is sensitive to light. On exposure to sunlight for only a few seconds, an impure IPBC takes on a yellow cast. The IPBC prepared by the process of the present invention, in stark contrast, remains white on exposure to light after many hours as a result of its greater purity.

By eliminating the use of an alcohol, such as methanol, in the aqueous reaction medium and by eliminating the use of a water immiscible organic solvent as an extractant for isolating the IPBC, not only are costs reduced, but both instability problems and severe environmental problems are avoided. Use of methanol and extraction solvents also require installation of expensive storage tanks, recovery stills and explosion proof equipment. Processes using methanol inevitably experience losses of methanol and solvent to the effluent and to the atmosphere.

The present invention provides a way of synthesizing iodoalkynyl carbamates, especially iodopropargyl carbamates, and particularly IPBC, in an aqueous solution, free of any co-solvents, that can be isolated in high yield and high purity without the need for water immiscible organic extractants.

BRIEF DESCRIPTION OF THE INVENTION

The process of the present invention comprises a method for preparing an iodoalkynyl carbamate, particularly an iodopropargyl carbamate, and especially IPBC, in water free of any organic co-solvent. Iodoalkynyl carbamates have the following generic formula:

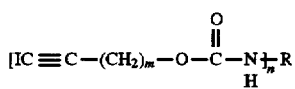

Wherein R is generally selected from the group consisting of hydrogen, substituted and unsubstituted alkyl groups having from 1 to 20 carbon atoms, substituted and unsubstituted aryl, alkylaryl, and aralkyl groups having from 6 to 20 carbon atoms and substituted and unsubstituted cycloalkyl and cycloalkynyl groups of 3 to 10 carbon atoms, and m and n are independently integers from 1 to 3, i.e., m and n are not necessarily the same.

Particularly preferred are the iodopropargyl carbamates where m is 1 and n is 1 having the following formula:

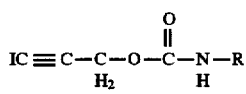

Suitable R substituents include alkyls such as methyl, ethyl, propyl, n-butyl, t-butyl, pentyl, hexyl, heptyl, octyl, nonyl, decyl, dodecyl, octadecyl, cycloalkyls such as cyclohexyl, aryls, alkaryls and aralkyls such as phenyl, benzyl, tolyl, cumyl, halogenated alkyls and aryls, such as chlorobutryl and chlorophenyl, and alkoxy aryls such as ethoxyphenyl and the like.

Especially preferred are such iodopropargyl carbamates as 3-iodo-2-propynyl propyl carbamate, 3-iodo-2-propynyl butyl carbamate, 3-iodo-2-propynyl hexyl carbamate, 3-iodo-2-propynyl cyclohexyl carbamate, and 3-iodo-2-propynyl phenyl carbamate. 3-iodo-2-propynyl butyl carbamate is most preferred.

According to the inventive process, an alkynyl carbamate, and especially a propargyl alkyl or cycloalkyl carbamate, is dispersed in water using a suitable surfactant selected from the group consisting of an organic phosphate ester and a salt of a sulfated fatty alcohol, then an amount of iodine (as crystals or preferably as a powder) is added to the aqueous dispersion, followed by carefully adding a sodium hypochlorite solution to the aqueous dispersion to form a precipitated reaction product which is thereafter filtered and washed with water to recover the desired iodopropargyl carbamate in high yield and high purity.

DETAILED DESCRIPTION OF THE INVENTION

The present invention is especially directed to a process for producing iodopropargyl carbamates, and especially iodopropargyl alkyl and cycloalkyl carbamates, in an aqueous reaction medium free of organic co-solvents, i.e., a reaction medium consisting essentially of water and a particular type of surfactant. The first step of the process involves forming a dispersion of a propargyl carbamate in a reaction medium consisting essentially of an aqueous solution of a suitable surfactant, i.e., the surfactant dissolved in water.

The propargyl carbamate, especially a propargyl alkyl carbamate, starting material may be formed by reacting a propargyl alcohol with an isocyanate according to known technology. By varying the isocyanate reactant a variety of propargyl carbamates may be prepared, as is well known. Other ways for preparing propargyl carbamates will also be recognized by those skilled in the art. Known procedures for preparing the propargyl carbamates yield products having a carbamate product purity above about 98 percent by weight. For simplicity, the present invention will be described primarily with reference to propargyl butyl carbamate, such as prepared using butyl isocyanate, but its applicability to other alkynyl carbamates, and particularly other propargyl carbamates, will be well-understood by those skilled in the art from the following description.

An aqueous dispersion of the propargyl butyl carbamate is prepared by adding it, with agitation, into the aqueous solution of the surfactant. The surfactant solution can be prepared by dissolving a suitable surfactant in water, generally using an aqueous alkaline solution to facilitate solvation, e.g., a caustic soda (NaOH) solution. A 2–4% solution of caustic soda has proven to be suitable for facilitating the dissolution of the surfactant. Other materials for preparing an alkaline solution suitable for dissolving the surfactant include other alkali metal hydroxides.

A key discovery of the present invention is that only certain surfactants create a propargyl carbamate dispersion from which iodopropargyl carbamate can be subsequently produced and isolated in a high yield and a high purity. In particular, applicant has found that surfactants which can be successfully employed in an essentially aqueous synthesis of iodopropargyl carbamates are certain acidic, organic phosphate partial esters and the neutralization salts of sulfated fatty alcohols, such as sodium lauryl sulfate or triethanolamine lauryl sulfate.

The acidic organic phosphate partial esters can be prepared by reaction of a fatty alcohol with a polyphosphoric acid. The reaction typically is conducted to a constant acid value, upon the controlled addition of the phosphoric acid to the alcohol generally under a reduced pressure, with agitation and with control of the temperature (e.g., 100° to 150° C.). Phosphoric acid equivalents such as pyrophosphoric acid (which is equivalent to 105% orthophosphoric acid), tetraphosphoric acid (which is equivalent to 115% orthophosphoric acid) or phosphorus pentoxide (which is equivalent to 138% orthophosphoric acid) also may be used as the phosphoric acid source. The phosphoric acid also can be reacted with a polyol, such as pentaerythritol, glycerol, trimethylol propane and the like, and then ethoxylated to produce an equivalent class of esters. Importantly, acidic, organic phosphate partial esters are commercially available from several sources including, for example, Witco, Stephan Co., and Alkaril Chemicals.

The sulfated fatty alcohol salts are prepared by sulfating a fatty alcohol, such as with sulfuric acid for example, and then neutralizing the product with an inorganic (e.g., sodium carbonate) or organic (e.g., triethanolamine) base. As with the organic phosphate partial esters, the sulfated fatty alcohol surfactants also are commercially available, such as from Witco and Stephan Co.

An amount of surfactant sufficient for forming an aqueous dispersion of the propargyl carbamate is dissolved in water. A surfactant concentration in the aqueous solution within the range of about 0.5–2.0 weight percent generally is acceptable for preparing the propargyl carbamate dispersion, although both higher and lower amounts may be suitable in some cases. In any event, a suitable amount of surfactant in the aqueous reaction mixture can be determined by routine experimentation.

The propargyl carbamate then is added to the alkaline solution of the surfactant with sufficient agitation to form a fine dispersion. The amount of propargyl carbamate added to the aqueous surfactant solution should not exceed the quantity that forms a fine dispersion. Generally, an aqueous solution containing from about 5% (by weight) to about 15% (by weight) propargyl carbamate should be suitable. Again, to the skilled worker, determining a suitable amount of propargyl carbamate to disperse into the aqueous reaction mixture involves only routine testing. Thereafter, molecular iodine is added to the aqueous dispersion of the propargyl carbamate with agitation. All told, a slight molar excess of iodine is added to the dispersion based on the amount of propargyl carbamate. The iodine can be added in the form of iodine crystals, but preferably is added in the form of a powder to facilitate thorough mixing in the aqueous reaction medium.

During the addition of the iodine to the propargyl carbamate dispersion, it is important to maintain the temperature of the aqueous dispersion at a relatively low temperature, referred to as a sub-ambient temperature. Generally a temperature below about 20° C., and preferably below about 15° C. should be suitable. More preferably, a temperature below about 10° C. is used. Extremely low temperatures are not preferred, however, because very low temperatures cause an increase in the viscosity of the reaction medium that inhibits thorough mixing. Once the iodine has been completely dispersed in the aqueous phase, a sodium hypochlorite solution is added to the dispersion at a controlled rate and with agitation. The sodium hypochlorite is added in an approximately stoichiometric amount relative to the previously added iodine and facilities the completion of the iodination reaction.

It is important to maintain the reaction mixture at the sub-ambient temperature during the addition of the iodine and sodium hypochlorite to control the exothermic iodination reaction. One convenient way to accomplish such temperature control in a batch operation is to divide the total input of iodine and sodium hypochlorite into two or more, and preferably about four, separate additions, as illustrated by the subsequent examples. The rate of adding the iodine and hypochlorite to the aqueous dispersion, to a large extent, depends on the efficiency of the cooling system for maintaining the sub-ambient reaction temperature. The addition of the iodine and hypochlorite should be controlled so as to prevent the exothermic reaction from producing an undesirably high reaction temperature.

Following a suitable period to complete the iodination reaction following the addition of the iodine and hypochlorite, generally from about 10 minutes to about 2 hours, the product iodopropargyl carbamate can be recovered in a high yield and at a high purity from the aqueous reaction medium. The carbamate product is normally recovered by simply filtering the reaction mixture, washing the filter cake with water, one or more times, and then drying the washed cake.

The invention will be further described by reference to the following examples. These examples are intended to illustrate the salient features of the invention and should not be construed in any way as limiting the invention.

EXAMPLE 1

IPBC was prepared according to the following procedure. To a beaker, equipped with an agitator and a thermometer, and immersed in an ice bath, water (400 g.) and sodium hydroxide (12.5 g.) were added and agitated until the sodium hydroxide completely dissolved. The temperature then was lowered to 6°–8° C. Then, Cedephos FA - 600 (7.6 g.) (a complex organic phosphate ester in free acid form (CAS No. 900 4-80-2) available from Stephan Co.) was added and agitated until it was completely dissolved in the aqueous alkaline solution.

Propargyl butyl carbamate (46.6 g.) then was added to the aqueous solution and agitation was continued until complete dispersion was attained, the temperature being maintained at 6°–8° C. At this point, iodine (powered) (9.55 g.) was added to the dispersion and agitation was continued until the color of the reaction mixture appeared white. Thereafter, a sodium hypochlorite solution (13.2% NaOCl) (20 g.) was added to the dispersion and the mixture was agitated, again until the reaction mixture was white. The steps of iodine addition and sodium hypochlorite solution addition were then repeated two more times. Finally, one last addition of iodine (powdered) (9.5 g) followed by 10 minutes of agitation and the addition of sodium hypochlorite solution (13.2%) - (21 g.). After, agitating the reaction mixture for ½ hour, a 25% aqueous solution of $NaHSO_3$ (sodium bisulfite) can be used to remove unreacted iodine. At this point, the reaction mixture was filtered on a Buchner funnel and washed with three 250 cc. portions of water. The filter cake was broken into small pieces and dried overnight at 50° C. The product was a white solid consisting of iodopropynyl butyl carbamate. The overall yield from the starting propargyl carbamate was 91.4% and the purity of the product was determined by high performance liquid chromatography (HPLC) to be 98.44% by weight.

EXAMPLE 2

The procedure of Example 1 was repeated on a somewhat larger scale by dissolving NaOH (18g.) in 750 ml of water in a 1500 ml. beaker fitted with an agitator and a thermometer and immersed in an ice bath. Sodium lauryl sulfate (Stepanol WA available from Stephan Co.) (3.5 g.) then was added with agitation while continuing to cool the solution .until the sodium lauryl sulfate was dissolved and the solution was chilled to 17° C. At this point, propargyl butyl carbamate (46.5 g.) was added with agitation and after complete dispersion, iodine (12.7 g.) was stirred in for 15 minutes. Then, a sodium hypochlorite solution (12.6%) (33.5 g) was added with agitation. After 15 minutes, the iodine and NaOCL additions were repeated twice more, agitating the reaction mixture for 15 minutes between each addition. Finally, the mixture was agitated for one hour and then filtered. The filter cake was slurried in 600 ml. water and was filtered again. The filter cake was washed with 250 ml water. Following another filtration, the filter cake was dried overnight in an oven at 50° C. The isolated product, iodopropargyl butyl carbamate, was a white solid. The overall yield was 93.3%, at a purity (HPLC) of 98.2%. The amount of di-iodo compounds was 0.02%, and the triodo compounds 0.01%.

EXAMPLE 3

IPBC was prepared according to the following procedure. To a 2500 ml beaker, equipped with an agitator and a thermometer, and immersed in an ice bath, deionized water (750 ml.) and sodium hydroxide (18 g.) were added and agitated until the sodium hydroxide completely dissolved. Then, triethanolamine lauryl sulphate (4.0 g.) was added and agitated until it was completely dissolved. The aqueous mixture was then cooled to 15° C.

Propargyl butyl carbamate (46.5 g) then was added to the aqueous solution and agitation was continued until complete dispersion was attained, the temperature being maintained at 15° C. At this point, iodine (powered) (12.7 g.) was added to the dispersion and agitation was continued for 15 minutes. Thereafter, a sodium hypochlorite solution (12.6%) (33.5 g) was added to the dispersion and the mixture again was agitated for 15 minutes. The steps of iodine addition and sodium hypochlorite solution addition were then repeated two more times. After, agitating the reaction mixture for 1 hour, the reaction mixture was filtered on a Buchner funnel and washed with three 200 ml portions of water. At this point, the filter cake was dried at 50° C. in an oven for 18 hours. The recovered product was a white powder, containing 98.1% iodopropynyl butyl carbamate in a 92.4% overall yield. Polyiodo compounds were found to comprise only 0.015% of the product composition.

In the foregoing examples, the iodine was added to the reaction mixture in several steps. However, the iodine and sodium chlorite may be added in a single step, or in as many steps as required, by the cooling capacity of the reaction vessel utilized. Continuous operation also is possible.

EXAMPLE A

To a beaker (1500 ml), equipped with an agitator and a thermometer, and immersed in an ice bath, water (250 g.), sodium hydroxide (24.7 g.) and methanol (241.0 g) were added and agitated until completely dissolved and the temperature then was lowered to 8° C. Then, propargyl butyl carbamate (95.1 g.) was added to the aqueous methanol solution and agitation was continued until complete dispersion was attained, the temperature being maintained at 8° C. At this point, iodine (powered) (76.2 g.) was added to the reaction mixture and agitation was continued for 15 minutes. Thereafter, a sodium hypochlorite solution (13.7% NaOCl) (165 g.) was slowly added to the dispersion, to facilitate temperature control, and the mixture was agitated, maintaining the temperature at 8°–10° C. Agitation was continued and 525 ml of water was added to reduce the viscosity of the reaction mixture. After, agitating the reaction mixture for 10 additional minutes, the reaction mixture was filtered on a Buchner funnel and washed with three 300 ml. portions of water. The filter cake was dried in an oven for 20 hours at 50° C. The product was a white solid consisting of iodopropynyl butyl carbamate having a yield of about 84% and a purity (HPLC) of 96.7%, containing 0.42% polyiodinated compounds.

EXAMPLE B

To a beaker (1500 ml), equipped with an agitator and a thermometer, and immersed in an ice bath, water (400 g.) and sodium hydroxide (12.5 g.) were added and agitated until the sodium hydroxide completely dissolved. Then, Cremophor El (16 g.) (an ethoxylated castor oil available from BASF) was added and agitated until it was completely dissolved. Once the solution was cooled to 8°–10° C., propargyl butyl carbamate (46.6 g.) was added to the aqueous solution and agitation was continued until complete dispersion was attained. At this point, iodine (powered) (9.55 g.) was added to the dispersion and agitation was continued for 15 minutes. Thereafter, a sodium hypochlorite solution (13.2% NaOCl) (20 g.) was added to the dispersion and the mixture was agitated, again for 15 minutes. The steps of iodine addition and sodium hypochlorite solution addition were then repeated two more times. Isolation of the iodopropynyl butyl carbamate was accomplished with great difficulty by filtration and washing with a solution of Cremophor El in water. The reaction mixture consisted of a white precipitate incorporated within a considerable amount of a dark oil that consisted apparently of a solution of iodine in propynylbutyl carbamate. The yield was only 61%. The purity could not be ascertained in a meaningful manner.

EXAMPLE C

The procedure of Example B was repeated, using a combination of Cremophor El, (8 g). and Dowfax 2A-1 (15 g) (a 45% solution of an alkylated diphenyl oxide disulfonate of average molecular weight 576, available from Dow Chemical) as the surfactant. The result was similar to that of Example B, but the yield was 73% of an off-white tacky mass of powder.

It will be apparent to those skilled in the art that various modifications and variations can be made in the compositions and methods of the present invention without departing from the spirit or scope of the invention. Thus, it is intended that the present invention cover the modifications and variations of this invention provided they come within the scope of the appended claims and their equivalents.

What is claimed is:

1. A method for preparing an iodoalkynyl carbamate in high yield and high purity which comprises dispersing an alkynyl carbamate in a reaction medium consisting essentially of an aqueous solution of a surfactant, said surfactant selected from the group consisting of an acidic organic phosphate partial ester and a salt of a sulfated fatty alcohol, followed by iodinating the dispersed alkynyl carbamate in said reaction medium with iodine and sodium hypochlorite.

2. The method of claim 1 wherein the surfactant is selected from the group consisting of sodium lauryl sulfate and triethanolamine lauryl sulfate.

3. The method of claim 1 wherein the aqueous solution of said surfactant is prepared by dissolving the surfactant in an aqueous alkaline solution.

4. The method of claim 3 wherein the aqueous alkaline solution is a solution of an alkali metal hydroxide.

5. The method of claim 1 wherein the alkynyl carbamate is a propargyl carbamate.

6. The method of claim 5 wherein the propargyl carbamate is a propargyl alkyl carbamate.

7. The method of claim 6 wherein the propargyl alkyl carbamate is propargyl butyl carbamate.

8. The method of claim 1 wherein said iodinating is conducted at a temperature of below about 20° C.

9. The method of claim 1 wherein said iodinating is conducted at a temperature of below about 10° C.

10. A method for preparing an iodoalkynyl carbamate of the following formula and in high yield and high purity:

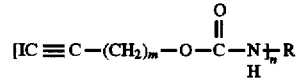

wherein R is selected from the group consisting of hydrogen, substituted and unsubstituted alkyl groups having from 1 to 20 carbon atoms, substituted and unsubstituted aryl, alkylaryl, and aralkyl groups having from 6 to 20 carbon atoms and substituted and unsubstituted cycloalkyl and cycloalkynyl groups of 3 to 10 carbon atoms, and m and n are independently integers from 1 to 3 which comprises dispersing an alkynyl carbamate in a reaction medium consisting essentially of an aqueous solution of a surfactant, said surfactant selected from the group consisting of an acidic organic phosphate partial ester and a salt of a sulfated fatty alcohol, followed by iodinating the dispersed alkynyl carbamate in said reaction medium with iodine and sodium hypochlorite.

11. A method for preparing an iodopropargyl carbamate of the following formula and in high yield and high purity:

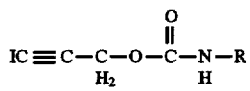

wherein R is selected from the group consisting of hydrogen, substituted and unsubstituted alkyl groups having from 1 to 20 carbon atoms, substituted and unsubstituted aryl, alkylaryl, and aralkyl groups having from 6 to 20 carbon atoms and substituted and unsubstituted cycloalkyl and cycloalkynyl groups of 3 to 10 carbon atoms, which comprises dispersing an alkynyl carbamate in a reaction medium consisting essentially of an aqueous solution of a surfactant, said surfactant selected from the group consisting of an acidic organic phosphate partial ester and a salt of a sulfated fatty alcohol, followed by iodinating the dispersed alkynyl carbamate in said reaction medium with iodine and sodium hypochlorite.

12. The method of claim 7 wherein the iodopropargyl carbamates is selected from the group consisting of 3-iodo-2-propynyl propyl carbamate, 3-iodo-2-propynyl butyl carbamate, 3-iodo-2-propynyl hexyl carbamate, 3-iodo-2-propynyl cyclohexyl carbamate, and 3-iodo-2-propynyl phenyl carbamate.

13. A method for preparing an iodoalkynyl carbamate selected from the group consisting of 3-iodo-2-propynyl propyl carbamate, 3-iodo-2-propynyl butyl carbamate, 3-iodo-2-propynyl hexyl carbamate, 3-iodo-2-propynyl cyclohexyl carbamate, and 3-iodo-2-propynyl phenyl carbamate in high yield and high purity which comprises dispersing 5 to 15 weight percent of an alkynyl carbamate in a reaction medium consisting essentially of an aqueous solution containing 0.5 to 2.0 weight percent of a surfactant, said surfactant selected from the group consisting of an acidic organic phosphate partial ester and a salt of a sulfated fatty alcohol, followed by iodinating the dispersed alkynyl carbamate in said reaction medium with iodine and sodium hypochlorite at a temperature below about 15° C.

* * * * *

UNITED STATES PATENT AND TRADEMARK OFFICE
CERTIFICATE OF CORRECTION

PATENT NO. : 5,693,849  
DATED : December 2, 1997  
INVENTOR(S) : Milton Nowak

Page 1 of 2

It is certified that error appears in the above-identified patent and that said Letters Patent is hereby corrected as shown below:

On the title page, "13 claims" should read --18 claims--.

--14. A method for preparing an iodoalkynyl carbamate in high yield and high purity which comprises dispersing an alkynyl carbamate in a reaction medium consisting essentially of an aqueous solution of a surfactant, said surfactant selected from the group consisting of an acidic organic phosphate partial ester and a salt of a sulfated fatty alcohol, followed by iodinating the dispersed alkynyl carbamate in said reaction medium with iodine and sodium hypochlorite and recovering said iodoalkynyl carbamate by filtering said reaction medium.

15. The method of claim 14 wherein said iodoalkynyl carbamate has the following formula:

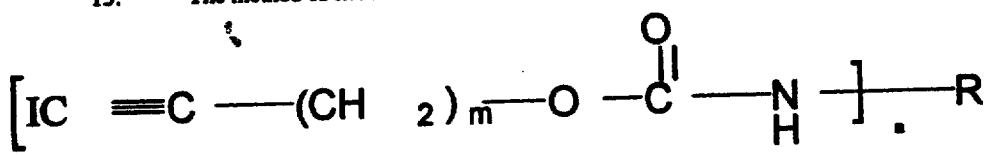

wherein R is selected from the group consisting of hydrogen, substituted and unsubstituted alkyl groups having from 1 to 20 carbon atoms, substituted and unsubstituted aryl, alkylaryl, and aralkyl groups having from 6 to 20 carbon atoms and substituted and unsubstituted cycloalkyl and cycloalkynyl groups of 3 to 10 carbon atoms, and m and n are independently integers from 1 to 3.

UNITED STATES PATENT AND TRADEMARK OFFICE
CERTIFICATE OF CORRECTION

PATENT NO. : 5,693,849
DATED : December 2, 1997
INVENTOR(S) : Milton Nowak

It is certified that error appears in the above-identified patent and that said Letters Patent is hereby corrected as shown below:

16. The method of claim 15 wherein the iodoalkynyl carbamate is selected from the group consisting of 3-iodo-2-propynyl propyl carbamate, 3-iodo-2-propynyl butyl carbamate, 3-iodo-2-propynyl hexyl carbamate, 3-iodo-2-propynyl cyclohexyl carbamate, and 3-iodo-2-propynyl phenyl carbamate.

17. A method for preparing an iodoalkynyl carbamate in high yield and high purity which comprises dispersing 5 to 15 weight percent of an alkynyl carbamate in a reaction medium consisting essentially of an aqueous solution containing 0.5 to 2.0 weight percent of a surfactant and free of organic co-solvent, said surfactant selected from the group consisting of an acidic organic phosphate partial ester and a salt of a sulfated fatty alcohol, followed by iodinating the dispersed alkynyl carbamate in said reaction medium with iodine and sodium hypochlorite at a temperature below about 20°C and recovering said iodoalkynyl carbamate by filtering said reaction medium.

18. The method of claim 17 wherein the iodoalkynyl carbamate is selected from the group consisting of 3-iodo-2-propynyl propyl carbamate, 3-iodo-2-propynyl butyl carbamate, 3-iodo-2-propynyl hexyl carbamate, 3-iodo-2-propynyl cyclohexyl carbamate, and 3-iodo-2-propynyl phenyl carbamate.--

Signed and Sealed this

Fourteenth Day of April, 1998

BRUCE LEHMAN

*Attest:*

*Attesting Officer*                *Commissioner of Patents and Trademarks*